United States Patent
Martin et al.

(10) Patent No.: US 7,375,358 B1
(45) Date of Patent: *May 20, 2008

(54) RADIATION SHIELD FOR PORTABLE X-RAY FLUORESCENCE INSTRUMENTS

(75) Inventors: Kenneth P. Martin, Watertown, MA (US); Anthony Honnellio, Billerica, MA (US); Lee Grodzins, Lexington, MA (US)

(73) Assignee: Thermo NITON Analyzers LLC, Billerica, MA (US)

( * ) Notice: Subject to any disclaimer, the term of this patent is extended or adjusted under 35 U.S.C. 154(b) by 130 days.

This patent is subject to a terminal disclaimer.

(21) Appl. No.: 11/115,977

(22) Filed: Apr. 27, 2005

Related U.S. Application Data

(63) Continuation-in-part of application No. 10/852,337, filed on May 24, 2004, now Pat. No. 6,965,118.

(60) Provisional application No. 60/472,674, filed on May 22, 2003.

(51) Int. Cl.
*G01N 23/223* (2006.01)

(52) U.S. Cl. .................................. 250/515.1

(58) Field of Classification Search ............ 250/515.1, 250/505.1; 378/44–50, 145
See application file for complete search history.

(56) References Cited

U.S. PATENT DOCUMENTS

| 3,353,023 | A | | 11/1967 | Lowery et al. | |
|---|---|---|---|---|---|
| 4,415,804 | A | | 11/1983 | Sowerby | 250/255 |
| 5,740,223 | A | * | 4/1998 | Ozawa et al. | 378/161 |
| 6,256,373 | B1 | | 7/2001 | Bernstein et al. | 378/45 |
| 6,765,986 | B2 | * | 7/2004 | Grodzins et al. | 378/46 |
| 6,909,770 | B2 | * | 6/2005 | Schramm et al. | 378/45 |
| 6,965,118 | B2 | * | 11/2005 | Martin et al. | 250/515.1 |
| 6,965,663 | B2 | * | 11/2005 | Ohzawa | 378/44 |
| 2002/0148980 | A1 | | 10/2002 | Cadwalader et al. | 250/515.1 |

FOREIGN PATENT DOCUMENTS

| EP | 0 781 992 | 7/1997 |
|---|---|---|
| WO | WO 00/37928 | 6/2000 |

OTHER PUBLICATIONS

Afshari et al., "Quantitative Measurement of Lead in Paint by XRF Analysis Without Manual Substrate Correction", Applied Radiation and Isotopes, Pergamon Press, Ltd., vol. 48, No. 1012, pp. 1425-1431, Oct. 11, 1997.

* cited by examiner

*Primary Examiner*—Kiet T. Nguyen
(74) *Attorney, Agent, or Firm*—Bromberg & Sunstein LLP

(57) ABSTRACT

A radiation shield and method for reducing ambient radiation levels at a distance from a surface irradiated by penetrating radiation emanating from an instrument substantially along a propagation axis. The shield attaches to an end of the instrument proximate to an irradiated surface and has a surface of attenuating material disposed with a component extending outward from the propagation axis of penetrating radiation and substantially adjacent to the irradiated surface.

11 Claims, 3 Drawing Sheets

RADIATION SHIELD FOR PORTABLE X-RAY FLUORESCENCE INSTRUMENTS

The present application is a Continuation-in-Part of U.S. patent application Ser. No. 10/852,337, filed May 24, 2004, now allowed, which claims priority from U.S. Provisional Patent Application Ser. No. 60/472,674, filed May 22, 2003, as does the present application. The foregoing applications are incorporated herein by reference.

TECHNICAL FIELD

The present invention relates to methods and devices for minimizing ambient radiation when a portable x-ray instrument is taking measurements.

BACKGROUND ART

X-ray fluorescence (XRF) instruments measure properties of material by irradiating the material with x-rays or gamma rays and analyzing the fluorescent radiation to determine specified properties. The term "x-rays", as used herein and in any appended claims, refers to radiation that is generated either by radioactive sources, or by instruments such as x-ray tubes, and encompasses within the term all forms of penetrating radiation including gamma rays. The specified properties to be determined may include the elemental composition of the irradiated object, or the distribution of a particular element in the near surface of the object, or the density of the object, or the morphology.

XRF instruments typically have collimated beams and appropriate shielding so that the operator is not subjected to undue ionizing radiation. For example, laboratory XRF instruments typically require the operator to completely cover the instrument and the sample so that negligible radiation emanates from the XRF instrument.

Portable XRF instruments have special radiation shielding requirements since their use typically requires that the operator hold the instrument while making the measurements. The ambient radiation levels are a primary concern. The operator and any nearby people must not be subject to undue levels of ionizing radiation. XRF instruments that inspect houses for lead paint are one specific embodiment of this invention and offer a good example of its need.

Portable XRF instruments are now the choice for quantitative determinations of the concentration of lead in painted walls of a house. Commercial portable XRF lead-paint instruments use either radioactive sources, such as $^{109}$Cd and $^{57}$Co, or x-ray tubes to generate the fluorescing radiation that excite the lead atoms in the painted surfaces. The intensity of the fluoresced characteristic x-rays of lead gives measure to its concentration and allows the inspector to determine whether the paint is out of compliance with established regulatory limits.

The allowable ambient radiation levels differ from country to country. The United States regulations place restrictions on the radiation levels in the ambient space directly behind the instrument's x-ray exit port. Of special concern is the space where the operator may have his hands or face. Minimal attention is paid to the radiation levels in the space between the wall being inspected and the surfaces of the operator's hands, arms and body when taking the measurements. The radiation limitations in the US can be satisfied by applying shielding in the instrument itself.

Radiation limitations in Europe are currently significantly more stringent than those in the United States. The acceptable level of radiation for an occupation worker is ten times lower; that is, 1 μSv/hr for Europe and 10 μSv/hr for the US. (μSv/hr is the standard abbreviation for microSievert per hour, a level of radiation equivalent to 100 microrem of radiation in now obsolete units.) Moreover, and of special importance to this invention, France requires that no point 10 cm from any accessible surface of the XRF instrument exceed the 1 μSv/hr level. That requirement cannot be satisfied with the shielding inside an XRF instrument.

Commercial hand-held x-ray fluorescing instruments have radiation absorbing material in the nose of the instrument. This absorbing material is designed to absorb radiation that comes directly from the source but is not going out through the exit port to strike the sample under study. This absorbing material also absorbs radiation that has been once-scattered so that the once-scattered radiation does not enter the detector and does not confound the measurement being made. The absorbing material in the nose of the inspection instrument, however, cannot prevent radiation that is multiply scattered such that it emerges from the target in a place and direction in such a way as to not intersect the nose of the instrument.

SUMMARY OF THE INVENTION

In accordance with preferred embodiments of the invention, a radiation shield is provided, consisting of a membrane containing material that absorbs ionizing radiation, the membrane being attached to the front face of the XRF instrument that emits penetrating radiation predominantly along a propagation axis and that is used for inspecting materials. The radiation shield extends outwardly from the propagation axis and may, for example, lie proximate to the walls being inspected. The membrane may be flexible enough so that it conforms to surfaces of the inspected walls and the membrane being of sufficient thickness to reduce radiation levels to below levels required for radiation safety.

More particularly, the radiation shield may reduce ambient radiation levels at a distance from a surface irradiated by penetrating radiation emanating from an instrument that has a distal end proximate to the irradiated surface and emitting the penetrating radiation predominantly along a propagation axis. The radiation shield has a platen of attenuating material having an extent substantially transverse to the propagation direction of penetrating radiation and substantially adjacent to the irradiated surface.

In accordance with further embodiments of the invention, the attenuating material may be a metal of atomic number greater than 45 embedded in a polymer matrix. The platen of attenuating material may be coupled to the instrument by means of fasteners, and may be detachable from the instrument. The platen may also have outer layers of an elastomer, and the platen may be sized such that ionizing radiation that has interacted multiple times with the irradiated surface is attenuated by the radiation shield prior to propagation through the ambient environment.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS OF THE INVENTION

Figure 1:
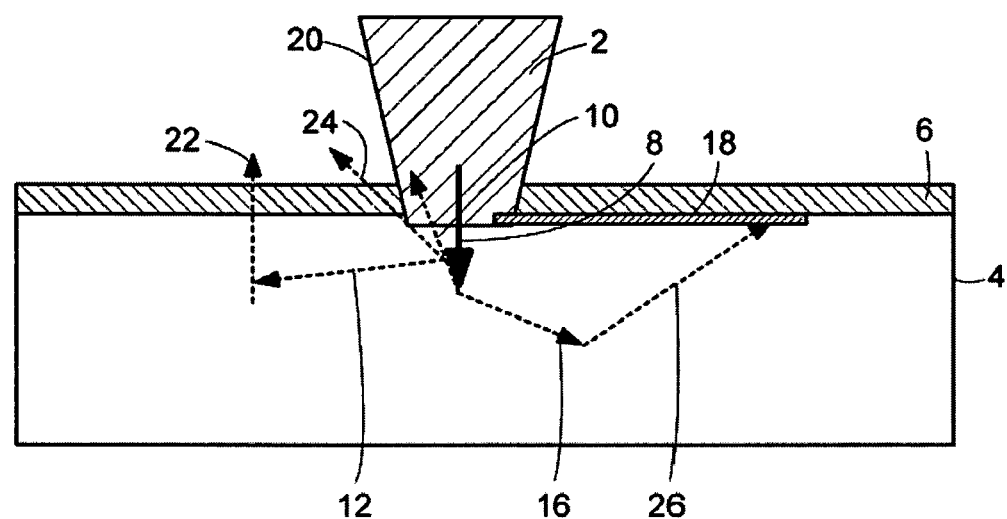
FIG. 1 depicts basic elements for discussing ambient radiation from portable XRF instruments and shows a radiation shield in accordance with an embodiment of present invention.

In accordance with embodiments of the present invention, and as described now with reference to FIG. 1, shielding in the form of a collar is used to prevent multiple scattered x-rays from exiting the wall relatively far from the XRF instrument with sufficient intensity to exceed regulatory limits.

To fully appreciate why the present invention is needed and how it must be designed we need to understand the origin of the ambient radiations that result when a beam of x-rays enters material and gets Compton scattered.

The Physics of Ambient Radiation

The following discussion refers particularly to an XRF instrument used for lead paint analysis, however it should be appreciated that the conclusions drawn, and the invention described, are applicable to a wide group of applications, especially the XRF analysis of soils and plastics.

The energies of the x-rays that fluoresce lead are typically in the 20 keV range when the L x-rays of lead at 10.5 keV and 12.6 keV are used for the analysis, and above 88 keV when the K x-ray lines, at 72.8 keV and 75 keV, are used for the analysis. In the following description we will restrict ourselves to fluorescing energies of 22.2 keV (from $^{109}$Cd) used to excite the L lines, and 122 keV (from $^{57}$Co) used to excite the K lines. It is to be understood, however, that these particulars are presented by way of illustration and not by way of limitation.

Referring to FIG. 1, an instrument 2, shown as a trapezoid, is depicted in a position abutting a wall 4. Instrument 2 emits penetrating radiation predominantly along a propagation axis designated by arrow 8 (which numeral also designates the emitted x-rays) and will be discussed herein as an XRF instrument 2 that emits x-rays 8. X-rays 8 exit from the XRF instrument, and enter a paint layer 6 on wall 4. Some of the x-rays 10 fluoresce or scatter back into the instrument 2 to either be counted in the detector (not shown) of XRF instrument 2 or absorbed by the walls 20 of the instrument.

Some of the x-rays 24, scatter backwards out of the wall, and miss the XRF instrument. Many x-rays, 12 and 16, however, scatter into the wall material itself. And some of those that scatter into the wall material scatter again resulting in x-rays 22 and 26 that exit the painted wall at a considerable distance from the XRF instrument 2.

The relative intensity of the x-rays that exit the wall in this way depends on the angular distributions of the Compton scattering, the energies of the scattered radiations and the distances the scattered radiations travel in the material of the wall between interactions. As we describe below, the scattering is, within a factor of about 2, isotropic; the energy of the scattered x-rays are almost as high as the incident energy; and the distance that the x-ray cascade travels in the wood before dissipating can be many centimeters. Therefore, shielding, as described herein, is desirable to reduce the levels of radiation to which a user is exposed to within specified safety levels, such as those enumerated above.

The angular distributions of Compton scattering for the x-rays of interest in XRF are similar to the distributions of Thompson (classical) scattering. The probability of Thompson scattering through an angle $\theta$ is proportional to $(1+\cos^2\theta)$. The intensity of backscattering is equal to that of forward scattering and side scattering is half as strong. The scattering of 22 keV x-rays follows the Thompson formula within a few percent. The Compton scattering of 122 keV x-rays is more forward peaked but side scatter and back scatter remain very probable.

The change in the energy of the x-rays when scattered through a particular angle $\theta$ depends strongly on the x-ray energy. A 22 keV x-ray scattered through 90° only loses 1 keV to the scattering electron so that the scattered x-rays has 21 keV. A 122 keV x-ray scattered through 90° loses about 24 keV and ends up being 98 keV.

The distance that the x-rays travel in the wall medium depends strongly on the composition of the medium. It is useful to measure that distance in mean free paths (MFP). The mean free path for an incident x-ray is the distance a beam of the x-rays will travel in the medium before the intensity of the incident x-ray has dropped by a factor of 2.718. The intensity of the incident beam may drop because x-rays have been absorbed by the photo-electric effect, in which case the x-rays will not contribute to ambient radiation.

The photoelectric effect result in secondary x-rays generated when the photoelectric excited atom relaxes to its ground state. These characteristic x-rays can be intensive enough in special circumstances to add significantly to the ambient radiation. These secondary x-rays may also advantageously be absorbed by the radiation shield that is described herein. Additionally, radiation shield 18 may also advantageously block singly scattered x-rays such as those designated by numeral 24.

If the intensity of the incident beam drops because of scattering, then the incident x-ray has simply been transformed into a lower energy x-ray traveling in a new direction and it can still contribute to ambient radiation.

Table 1 gives the mean free paths of the 22 keV and the 122 keV x-rays, and the energies of the x-rays of 21 keV and 98 keV after a 90° scattering. The materials are air, wood, plaster, aluminum, and iron.

TABLE 1

Mean Free Paths in Centimeters

|  | 22 keV | 21 keV | 122 keV | 98 keV |
| --- | --- | --- | --- | --- |
| air | 1756 | 1592 | 5455 | 5162 |
| wood | 3.59 | 3.26 | 11.11 | 10.55 |
| brick | 0.28 | 0.24 | 3.42 | 3.13 |
| aluminum | 0.15 | 0.13 | 2.59 | 2.33 |
| iron | 0.07 | 0.06 | 0.54 | 0.36 |

The mean free paths for 22 keV radiations are many meters in air, several centimeters in wood and several millimeters or less in heavy materials that make up common walls. The 122 keV radiations used to excite the K lines of lead go several to many centimeters in all common wall material but steel.

Table 2, which gives the probability that an x-ray will be scattered at least once in traversing the material before being absorbed gives further insight into what is happening.

TABLE 2

Probability that the X-ray will be Scattered at Least Once

|  | 22 keV | 21 keV | 122 keV | 98 keV |
|---|---|---|---|---|
| air | 40% | 33% | 99.6% | 98.6% |
| wood | 40% | 33% | 99.3% | 98.5% |
| brick | 8% | 7% | 95% | 91% |
| aluminum | 6% | 5% | 93% | 87.5% |
| iron | 0.6% | 0.5% | 52% | 38% |

From Table 1 it is apparent that any 22 keV x-rays that pass through the paint into the wooden will travel several centimeters before interacting. And when a 22 keV x-ray does interact, there is 40% probability that the x-ray will scatter and not be absorbed. Furthermore, there is a strong probability that the scattering will be to side. Those side-scattered x-rays will have almost the same energy as the incident energy and will themselves travel several centimeters before interacting. And again the probability of scattering is high. It is easy to see that a significant amount of radiation can escape from the wood on the sides of the XRF instrument.

Materials with higher atomic number and greater density than wood present much less of a problem because, as Table 1 and Table 2 show, the x-rays do not travel far in these materials and they quickly get absorbed.

Table 1 and Table 2 also show why K-shell XRF analyzers that measure the lead concentration by studying the K lines have a far more difficult time controlling the ambient radiation. Scattering completely dominates over absorption except for steel walls and the scattered radiations can travel 10 cm in wood before interacting.

Figure 2:
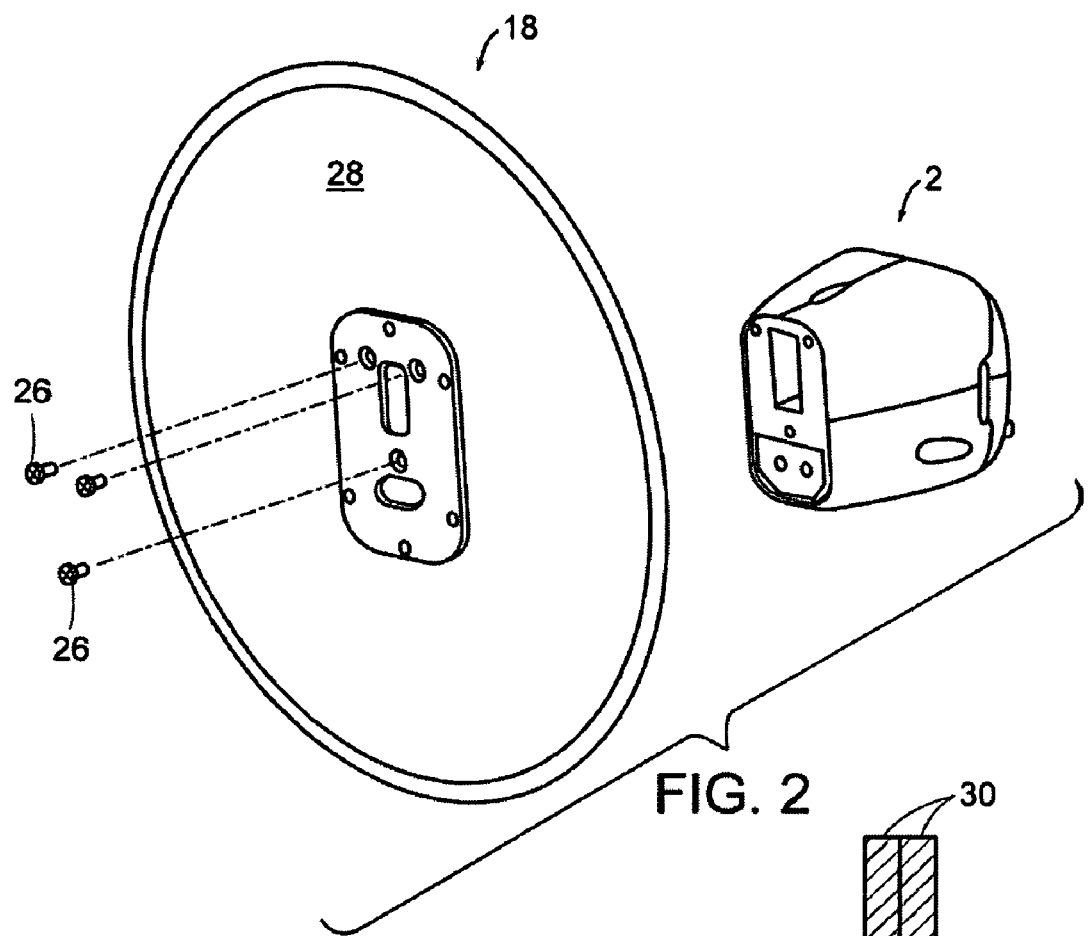
FIG. 2 is a perspective view of a radiation shield, in accordance with an embodiment of the present invention, depicting, in an exploded format, its attachment to an XRF instrument.
Figure 3:
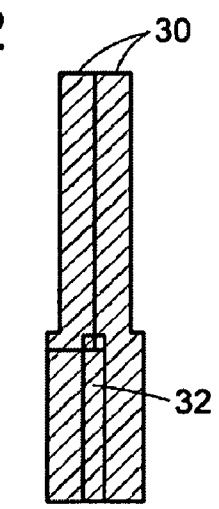
FIG. 3 is a cross-section of a radius of the radiation shield of FIG. 2, showing the a laminated shield structure.

One embodiment of a radiation shield, such as that depicted schematically in FIG. 1 by a heavy line designated by numeral 18, is shown in perspective view in FIG. 2. Radiation shield 18 is coupled to XRF instrument 2 by fasteners 26 which may include screw, rivets, clips, or any other fasteners. Radiation shield 18 may be readily detachable or exchangeable. In a preferred embodiment of the invention, radiation shield 18 has a platen 28 of shielding material, shown in cross-section in FIG. 3. The platen may be referred to herein as a 'membrane'. In a preferred embodiment, platen 28 is circular, and has a diameter of approximately 20 cm. Other shapes and sizes are within the scope of the present invention, for example, radiation shield 18 may extend outward conically from the propagation axis 8 (shown in FIG. 1). FIG. 3 shows a laminate formed of two layers of elastomer (such as rubber) with an included layer 32 of shielding material, such as a metal of high atomic number, typically greater than Z=45, embedded in a polymer matrix. Such metals may include tin, tungsten or lead. A preferred material is tungsten-filled polyvinyl chloride (PVC). The platen is preferably flexible to allow it to conform to contours of the abutted surface, such as to measure as close as possible to a corner, or to interrogate a niche in a wall such as the slide recess for a window.

Figure 4:
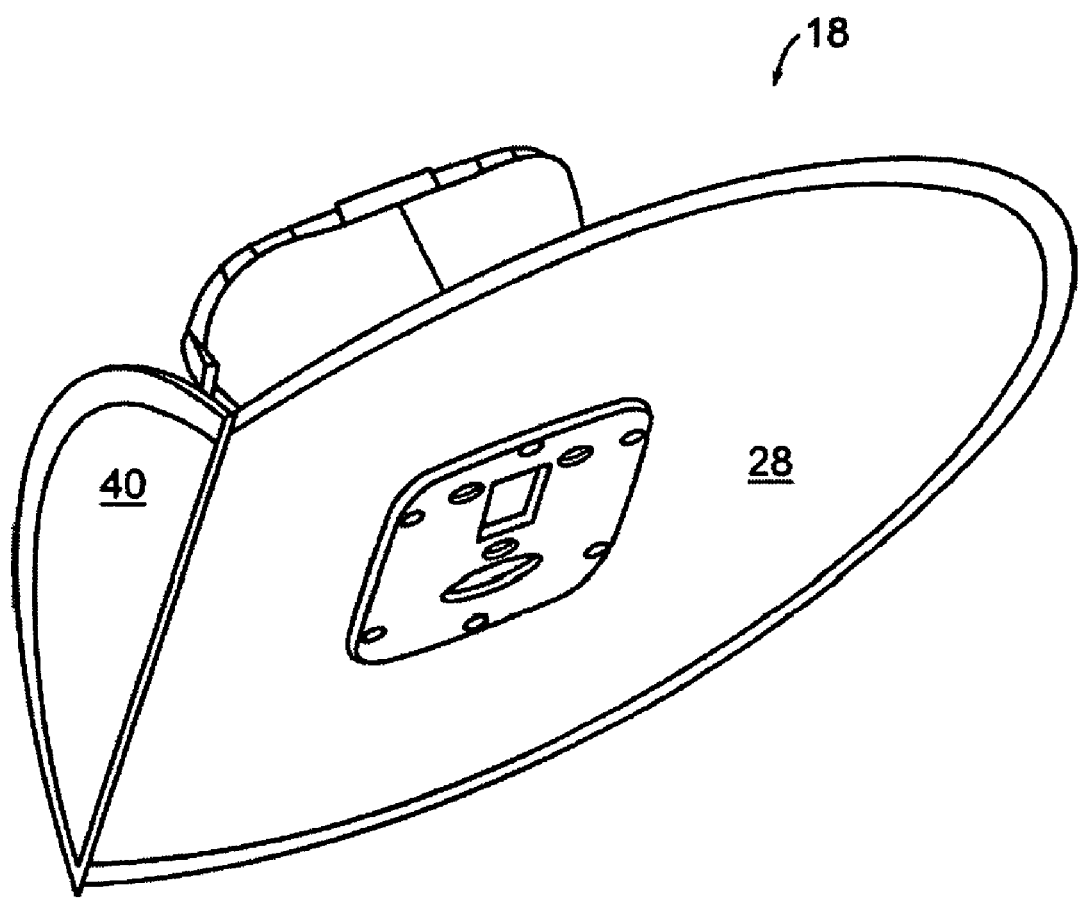
FIG. 4 is a perspective view from beneath of a radiation shield allowing for use of an XRF instrument in a corner.

In accordance with other embodiments of the invention, referring now to FIG. 4, a section 40 of radiation shield 18 may lie in a plane other than the major part of platen 28 in order to allow the radiation shield to be used, for example, in inside corners of walls. Non-coplanar section 40 may be coupled to the rest of platen 28 at a fixed bend, or, alternatively, by a hinge, all as well-known in the art.

The described embodiments of the invention are intended to be merely exemplary and numerous variations and modifications will be apparent to those skilled in the art. All such variations and modifications are intended to be within the scope of the present invention as defined in the appended claims.

We claim:

1. A method for reducing levels of ambient radiation at a distance from a surface irradiated by penetrating radiation emanating from an instrument and characterized by a propagation axis, the instrument characterized by a distal end proximate to the surface to be irradiated, the method comprising:

providing a radiation shield comprising a metal of atomic number greater than 45 embedded in a polymer matrix for reducing the intensity of ionizing radiation transmitted through the radiation shield to below specified levels; and coupling the radiation shield so as to extend outward from the propagation axis of the irradiating radiation in such a manner as to shield a user of the instrument from the ambient radiation being emitted from the surface.

2. A radiation shield for reducing levels of ambient radiation at a distance from a surface irradiated by penetrating radiation emanating from an instrument and characterized by a propagation axis, the instrument characterized by a distal end proximate to the surface to be irradiated, the radiation shield comprising:

a platen of attenuating material disposed having an extent substantially transverse to the propagation axis and substantially adjacent to the irradiated surface, wherein the attenuating material is a metal of atomic number greater than 45 embedded in a polymer matrix.

3. A radiation shield in accordance with claim 2, wherein the platen of attenuating material is coupled to the instrument by means of fasteners.

4. A radiation shield in accordance with claim 2, wherein the platen of attenuating material is detachable from the instrument.

5. A radiation shield in accordance with claim 2, wherein the platen of attenuating material comprises outer layers of an elastomer.

6. A radiation shield in accordance with claim 2, wherein the platen of attenuating material is sized such that ionizing radiation that has interacted multiple times with the irradiated surface is attenuated by the radiation shield prior to propagation through the ambient environment.

7. A method for reducing levels of ambient radiation at a distance from a surface irradiated by penetrating radiation emanating from an instrument and characterized by a propagation axis, the instrument characterized by a distal end proximate to the surface to be irradiated, the method comprising:

providing a radiation shield having outer elastomeric layers for reducing the intensity of ionizing radiation transmitted through the radiation shield to below specified levels; and coupling the radiation shield so as to extend outward from the propagation axis of the irradiating radiation in such a manner as to shield a user of the instrument from the ambient radiation being emitted from the surface.

8. A radiation shield for reducing levels of ambient radiation at a distance from a surface irradiated by penetrating radiation emanating from an instrument and characterized by a propagation axis, the instrument characterized by a distal end proximate to the surface to be irradiated, the radiation shield comprising:

a platen comprising attenuating material and two outer elastomeric layers disposed having an extent substantially transverse to the propagation axis and substantially adjacent to the irradiated surface.

9. A radiation shield in accordance with claim 8, wherein the platen is coupled to the instrument by means of fasteners.

10. A radiation shield in accordance with claim 8, wherein the platen is detachable from the instrument.

11. A radiation shield in accordance with claim 8, wherein the platen is sized such that ionizing radiation that has interacted multiple times with the irradiated surface is attenuated by the radiation shield prior to propagation through the ambient environment.

* * * * *